＝

US011535589B2

(12) United States Patent
Friedrich et al.

(10) Patent No.: US 11,535,589 B2
(45) Date of Patent: Dec. 27, 2022

(54) FLUORINATED TENSIDES

(71) Applicant: MERCK PATENT GMBH, Darmstadt (DE)

(72) Inventors: Reiner Friedrich, Seeheim-Jugenheim (DE); Fabian Koch, Pfungstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/347,424

(22) PCT Filed: Nov. 1, 2017

(86) PCT No.: PCT/EP2017/077946
§ 371 (c)(1),
(2) Date: May 3, 2019

(87) PCT Pub. No.: WO2018/083110
PCT Pub. Date: May 11, 2018

(65) Prior Publication Data
US 2019/0276397 A1    Sep. 12, 2019

(30) Foreign Application Priority Data
Nov. 3, 2016 (DE) .......................... 102016013066.0

(51) Int. Cl.
| C07C 323/12 | (2006.01) |
| C09D 7/63 | (2018.01) |
| C07C 317/18 | (2006.01) |
| C07F 9/09 | (2006.01) |
| C11D 1/00 | (2006.01) |
| C07C 321/14 | (2006.01) |

(52) U.S. Cl.
CPC .......... *C07C 323/12* (2013.01); *C07C 317/18* (2013.01); *C07C 321/14* (2013.01); *C07F 9/091* (2013.01); *C09D 7/63* (2018.01); *C11D 1/004* (2013.01)

(58) Field of Classification Search
CPC .................................................. C07C 317/18
USPC ......................................................... 568/35
See application file for complete search history.

(56) References Cited

U.S. PATENT DOCUMENTS

| 5,366,991 | A | 11/1994 | Bettarini et al. |
| 5,484,953 | A | 1/1996 | Marhold et al. |
| 8,008,358 | B2 | 8/2011 | Kirsch et al. |
| 9,115,062 | B2 | 8/2015 | Hierse et al. |
| 2007/0100193 | A1 | 5/2007 | Harmer et al. |
| 2010/0120980 | A1 | 5/2010 | Peng et al. |
| 2011/0088594 | A1 | 4/2011 | Claus et al. |
| 2011/0118428 | A1 | 5/2011 | Hierse et al. |
| 2013/0269568 | A1 | 10/2013 | Claus et al. |
| 2017/0121260 | A1 | 5/2017 | Friedrich et al. |
| 2017/0349760 | A1 | 12/2017 | Friedrich |

FOREIGN PATENT DOCUMENTS

| CN | 1097191 A | 1/1995 |
| CN | 106029630 A | 10/2016 |
| DE | 265398 A1 | 3/1989 |
| EP | 0590720 A1 | 4/1994 |
| JP | 57108061 | * 7/1982 |
| JP | 2009513634 A | 4/2009 |
| JP | 2012087092 | * 2/2012 |
| JP | 2012508745 A | 4/2012 |
| WO | 06072401 A1 | 7/2006 |
| WO | 07066496 A1 | 6/2007 |
| WO | 09149807 A1 | 12/2009 |
| WO | 10003567 A2 | 1/2010 |
| WO | 10149262 A1 | 12/2010 |
| WO | 11082770 A2 | 7/2011 |
| WO | 12084118 A1 | 6/2012 |
| WO | 15124290 A1 | 8/2015 |
| WO | 16096129 A1 | 6/2016 |

OTHER PUBLICATIONS

Machine translation of JP 57108061, 1982.*
Bayoudh et al. Polymer International (2000), 49(7), 703-711.*
International search report WO2017EP77946 dated Jan. 3, 2018 (pp. 1-4).
G. L. Kennedy, Jr.; J. L. Butenhoff; G. W. Olsen; J. C. O'Connor; A. M. Seacat; R. G. Perkins; L. B. Biegel; S. R. Murphy; D. G. F, Critical Reviews in Toxicology, vol. 34, 2004, pp. 351-384.
Robert I. Mccarthy,: Cytosolic C-S lyase activity in human kidney samples—relevance for the nephrotoxicity of halogenated alkenes in man ,Toxicology and Industrial Health, (1994), 10(1/2), 103-112.
Ishikawa, Nobuo et al, Preparation of heterocycles by use of hexafluoropropene, Nippon Kagaku Kaishi (1973), (3), 563-567.
Office Action in corresponding CN application No. 201780067605.4 dated Sep. 29, 2020 (pp. 1-10).
Koob et al;, "Metabolism of Hexafluoropropene . . . ", Drug Metabolism and Disposition 1990, 18, 6, 911-916.
Rice et al.; "Perfluorocarbon Phosphonic and Sulfonic Acids . . . " Inorganic Chemistry 1991, 30, 24, 4635-4638.
McCarthy et al., "Cttisikuc C-S Lyase . . . " Toxicology and Industrial Health 1994, 20, 1_2, 103-112.
English translation of Notice_of_Reasons_for_Refusal in corresponding JP 2019523598 dated Aug. 11, 2021 (pp. 1-6).

* cited by examiner

Primary Examiner — Ana Z Muresan
(74) Attorney, Agent, or Firm — Millen, White, Zelano and Branigan, P.C.; Harry B. Shubin

(57) ABSTRACT

The present invention relates to novel compounds containing fluorinated end groups, to the use thereof as surface-active substances, and to compositions comprising these compounds.

7 Claims, No Drawings

FLUORINATED TENSIDES

The present invention relates to novel compounds containing fluorinated end groups, to the use thereof as surface-active substances, and to compositions comprising these compounds.

Fluorosurfactants are an important constituent in industrial process chemicals. Owing to their persistence and toxicity, these materials are problematic for users and the environment. Fluorine-containing surfactants can be employed in a very wide variety of applications and contribute, for example, to improved wetting of surfaces. Thus, they are used, for example, as interface promoter or emulsifier or viscosity reducer in paints, coatings or adhesives. Classical fluorosurfactants are built up from long-chain, perfluorinated alkyl chains (C6-C8) and are regarded as potentially bioaccumulative and toxic. In general, however, fluorosurfactants contain perfluoroalkyl substituents, which are broken down in the environment by biological and other oxidation processes to give perfluoroalkanecarboxylic acids and -sulfonic acids. These are regarded as persistent and are in some cases suspected of causing health damage (G. L. Kennedy, Jr., J. L. Butenhoff, G. W. Olsen, J. C. O'Connor, A. M. Seacat, R. G. Perkins, L. B. Biegel, S. R. Murphy, D. G. Farrar, *Critical Reviews in Toxicology* 2004, 34, 351-384). In addition, longer-chain perfluoroalkanecarboxylic acids and -sulfonic acids accumulate in the food chain. Shorter-chain fluorine building blocks are more favourable with respect to their ecotoxicological profiles, but often exhibit worse properties in their areas of application. WO 2006/072401 and WO 2010/003567 describe surface-active compounds containing trifluoromethoxy groups. Further fluorosurfactants containing fluorinated alkyl groups are described in WO 2009/149807, WO 2010/003567, WO 2010/149262, WO 2011/082770, WO 2012/084118, WO 2015/124290 and WO 2016/096129.

Furthermore, there is a need for alternative surface-active substances which preferably do not break down on degradation to give long-chain persistent compounds. Novel compounds have now been found which are suitable as surface-active substances and preferably do not have one or more of the above-mentioned disadvantages. The present invention relates firstly to compounds of the formula (I)

$$(R^1—CHF—CF_2—Y—)_m spacer(X)_n \qquad (I)$$

where
$R^1$=a fluorinated, linear or branched alkyl group, optionally containing heteroatoms,
spacer=a single bond or a divalent organic group,
X=a hydrophilic group,
Y=S, SO or $SO_2$,
m is ≥1
and n is ≥1,
where compounds (A), (B) and (C) in which Rf=a perfluorinated alkyl group, optionally containing heteroatoms, and R'=H or C1-C4-alkyl are excluded (A)

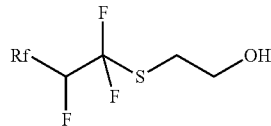

(B)

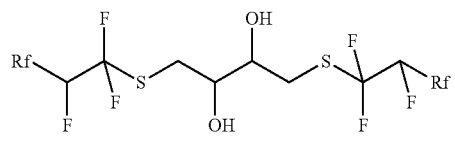

(C)

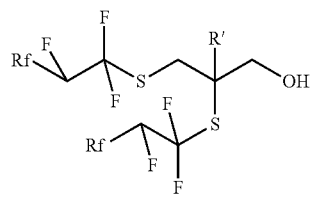

The compounds according to the invention preferably contain no —O—O— bonds. The novel compounds preferably contain the following variables:
$R^1$=perfluorinated alkyl, linear or branched, optionally containing heteroatoms, preferably perfluorinated C1-C6-alkyl, particularly preferably perfluorinated C1-C4-alkyl, in particular perfluorinated C1-C3-alkyl, spacer=a saturated or unsaturated, branched or unbranched hydrocarbon unit, optionally containing heteroatoms, where no —O—O— bonds are present,
X=an anionic, cationic, nonionic or amphoteric group,
Y=S, SO or $SO_2$, preferably S,
m=1, 2, 3, 4, 5 or 6, preferably 2-4, in particular 2-3, and
n=1, 2, 3 or 4, preferably 1 or 2.

Particularly preferred compounds of the formula (I) are those in which all variables have the preferred meanings.

The fluorinated group $R^1$ is preferably selected from the groups: $CF_3—(CF_2)_{0-3}—$, $CF_3—(CF_2)_{0-3}—O—$, $CF_3—(CF_2)_{0-3}—O—(CF_2)_{1-3}—$, $CF_3—(CF_2)_{0-3}—O—(CF_2)_{1-3}—O—$, $CF_3—(CF_2)_{0-3}—O—(CF_2)_{1-3}—O—CF_2—$, $CF_3—(CF_2)_{0-3}O—(CF_2—O)_{1-8}—$ and $CF_3—(CF_2)_{0-3}—O—(CF_2—O)_{1-8}—CF_2—$. The fluorinated group $R^1$ is particularly preferably a $CF_3—(CF_2)_{1-2}—O—$ group, in particular a $CF_3—CF_2—CF_2—O$ group.

A preferred anionic group X can be selected from $COO^-$, $—SO_3^-$, $—OSO_3^-$, $—PO_3^{2-}$, $—OPO_3^{2-}$, $—OP(O)(O^-)O—$, $—(OCH_2CH_2)_s—O—(CH_2)_t—COO^-$, $—(OCH_2CH_2)_s—O—(CH_2)_t—SO_3^-$, $—(OCH_2CH_2)_s—O—(CH_2)_t—OSO_3^-$, $—(OCH_2CH_2)_s—O—(CH_2)_t—PO_3^{2-}$, $—(OCH_2CH_2)_s—O—(CH_2)_t—OPO_3^{2-}$ or from the formulae A to C,

A

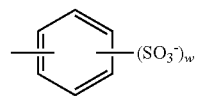

B

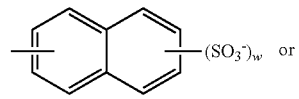

C

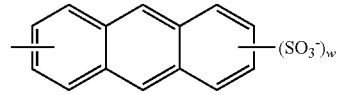

where s stands for an integer from the range from 1 to 1000, t stands for an integer selected from 1, 2, 3 or 4 and w stands for an integer selected from 1, 2 or 3.

The preferred anionic groups here include, in particular, —COO⁻, —SO₃⁻, —OSO₃⁻, —PO₃²⁻, —OPO₃²⁻, —OP(O)(O⁻)O—, sub-formula A, and —(OCH₂CH₂)$_s$—O—(CH₂)$_t$—COO⁻, —(OCH₂CH₂)$_s$—O—(CH₂)$_t$—SO₃⁻ and —(OCH₂CH₂)$_s$—O—(CH₂)$_t$—OSO₃⁻, where each one of these groups per se may be preferred. X may also stand for corresponding acids.

The very particularly preferred anionic groups here include —SO₃⁻, —OSO₃⁻, —COO⁻, —PO₃²⁻, —OP(O)(O⁻)O— or OPO₃²⁻. In particular, a sulfonate group —SO₃⁻ is preferred.

Preferred counterion for anionic groups X is a monovalent cation, in particular H⁺, an alkali-metal cation or $NR_4^+$, where R=H or C1-C6-alkyl and all R may be identical or different. Particular preference is given to H⁺, Na⁺, K⁺, Li⁺ and $NH_4^+$, especially preferably Na⁺.

A preferred cationic group X can be selected from —NR¹R²R³⁺Z⁻, —PR¹R²R³⁺Z⁻,

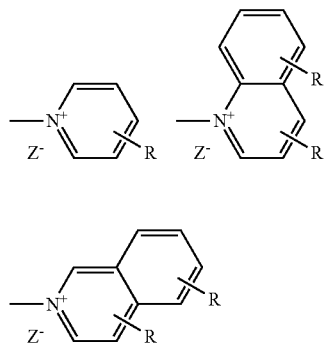

where R stands for H or $C_{1-4}$-alkyl in any desired position,

Z⁻ stands for Cl⁻, Br⁻, I⁻, CH₃SO₃⁻, CF₃SO₃⁻, CH₃PhSO₃⁻, PhSO₃⁻, R¹, R² and R³ each, independently of one another, stand for H, $C_{1-30}$-alkyl, Ar or —CH₂Ar and Ar stands for an unsubstituted or mono- or polysubstituted aromatic ring or condensed ring systems having 6 to 18 C atoms, in which, in addition, one or two CH groups may be replaced by N.

The preferred cationic groups here include, in particular, —NR¹R²R³⁺Z⁻ and

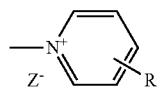

where each one of these groups per se may be preferred.

A preferred nonionic group X can be selected from: linear or branched alkyl, where one or more non-adjacent C atoms have been replaced by O, S, and/or N, —OH, —SH, —O-(glycoside)$_{o'}$, —S-(glycoside)$_{o'}$, —OCH₂—CHOH—CH₂—OH, —OCH₂Ar(—NCO)$_{p'}$, —OAr(—NCO)$_{p'}$, amine oxide,

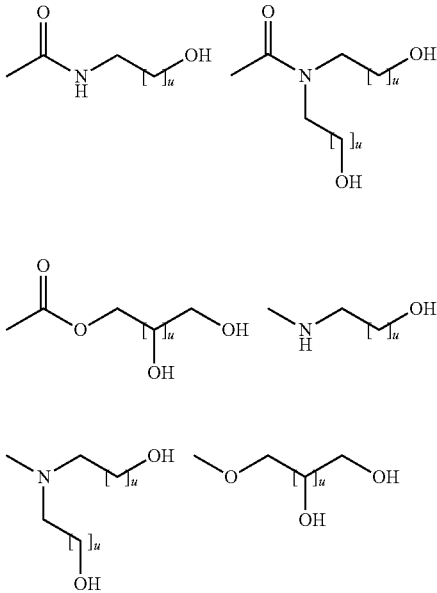

u stands for an integer from the range from 1 to 6, preferably 1 to 4, o' stands for an integer from the range from 1 to 10, p' stands for 1 or 2, Ar stands for an unsubstituted, mono- or polysubstituted aromatic ring or condensed ring systems having 6 to 18 C atoms, in which, in addition, one or two CH groups may be replaced by C=O and, glycoside stands for an etherified carbohydrate, preferably for a mono- di-, tri- or oligoglucoside.

The preferred nonionic groups X here include, in particular, linear or branched alkyl, where one or more non-adjacent C atoms have been replaced by O, S and/or N, —OH and —O-(glycoside)$_{o'}$.

If X=alkyl, where one or more non-adjacent C atoms have been replaced by O, S, and/or N, it is then preferably equal to $R^4$—(B-A)$_{m''}$- where $R^4$=H or C1-4-alkyl, in particular H or CH₃, A=linear or branched alkylene, preferably having 1 to 10 carbon atoms, in particular having 1 to 4 carbon atoms, B=O or S, preferably O, and m''=an integer preferably from the range from 1 to 100, particularly preferably 1 to 30.

The nonionic group X is particularly preferably the group $R^4$—(O—CH₂CHR⁵)$_{m''}$— where m''=an integer from the range from 1 to 100, preferably 1 to 30, in particular also 1-25, and $R^4$ and R⁵=H or C1-4-alkyl, in particular H or CH₃. $R^4$—(B-A)$_{m''}$- is particularly preferably a polyethylene glycol or polypropylene glycol unit.

The nonionic group X is particularly preferably the group —CH(OH)—CH₂—NH-sach where sach=various sugars and the group —Y—(CH₂—CH₂—O)$_v$—$R^4$ where Y=S, O or NH, preferably O, $R^4$=H or alkyl, preferably H or CH₃, and v=1-100, preferably 1-30, in particular also 1-25.

A preferred amphoteric group X can be selected from the functional groups of the acetyldiamines, the N-alkylamino acids, the N-alkylaminosulfonic acids, the betaines, the sulfobetaines, or corresponding derivatives, in particular selected from, where M stands for H or an alkali-metal ion, preferably Li⁺, Na⁺ or K⁺:

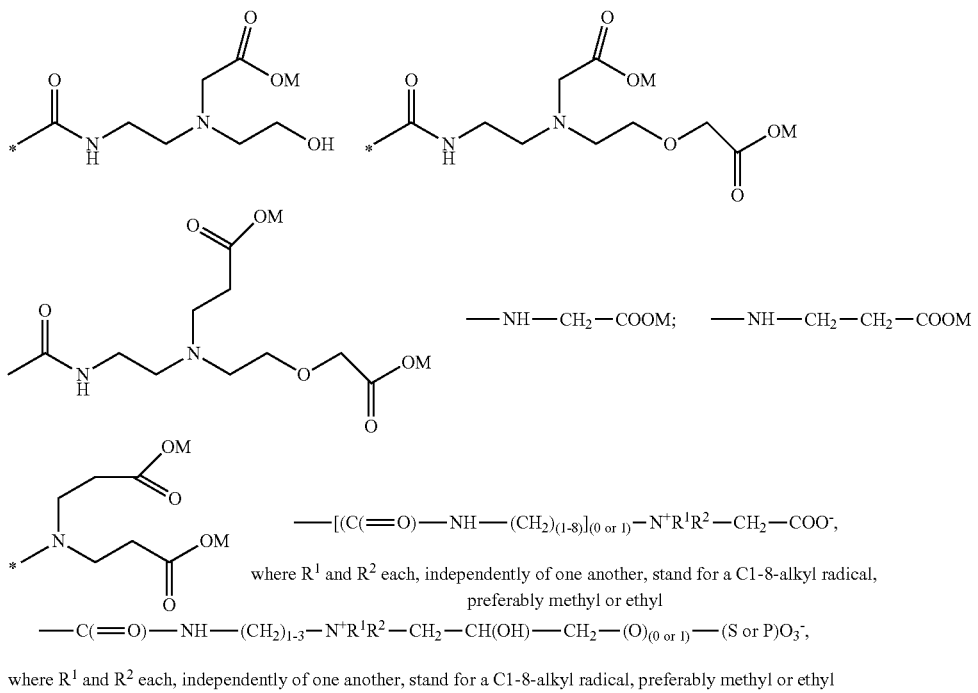

—NH—CH₂—COOM;   —NH—CH₂—CH₂—COOM

—[(C(=O)—NH—(CH₂)$_{(1-8)}$]$_{(0\ or\ 1)}$—N⁺R¹R²—CH₂—COO⁻, where R¹ and R² each, independently of one another, stand for a C1-8-alkyl radical, preferably methyl or ethyl —C(=O)—NH—(CH₂)$_{1-3}$—N⁺R¹R²—CH₂—CH(OH)—CH₂—(O)$_{(0\ or\ 1)}$—(S or P)O₃⁻, where R¹ and R² each, independently of one another, stand for a C1-8-alkyl radical, preferably methyl or ethyl Particularly preferred compounds according to the invention are those which contain, as hydrophilic group X, one of the preferred anionic groups, the preferred nonionic groups or the preferred zwitterionic groups. Particular preference is given to compounds which contain the groups —SO₃⁻, —OSO₃⁻, —COO⁻, —PO₃²⁻, —OP(O)(O⁻)O— or OPO₃²⁻, polyethylene glycols or polypropylene glycols, —CH(OH)—CH₂—NH-sach, —Y—(CH₂—CH₂—O)$_v$—R⁴, betaines, or sulfobetaines. Preferred counterions here are H⁺, Na⁺, K⁺ and NH₄⁺, in particular Na⁺. Particular preference is given to: —SO₃⁻, —COO⁻, —OP(O)(O⁻)O— or —OPO₃²⁻, polyethylene glycols or polypropylene glycols, sulfobetaines, the group —CH(OH)—CH₂—NH-sach and the group —Y—(CH₂—CH₂—O)$_v$—R⁴. Sach here=various sugars and Y=S, O or NH, preferably O, R⁴=H or alkyl, preferably H or CH₃, and v=1-100, preferably 1-30, in particular also 1-25. Compounds where X=—SO₃— may also be particularly advantageous.

The hydrocarbon units of the spacer of the compounds of the formula (I) can be aliphatic or aromatic units, optionally provided with heteroatoms. The spacer is preferably a saturated, branched or unbranched hydrocarbon unit, preferably a saturated branched or unbranched alkylene group, in which one or more non-adjacent C atoms may be replaced by O or N, preferably O, or connected to O. Preference is given, for example, to C1-C6-alkylene groups, in particular C1-C4-alkylene groups. In a variant of the invention, the preferred heteroatom-containing hydro-carbon unit used is a polyethylene glycol or polypropylene glycol unit.

Preference is given to compounds of the formulae (II) to (V) in which R¹ and R², independently of one another, are a fluorinated, linear or branched alkyl group, optionally containing heteroatoms, o=0-100, preferably 1-30 and 5-30, in particular 3, 5, 6, 10, 12, 15, 18, 20 or 24, and X¹ and X², independently of one another, are a hydrophilic group, in particular an anionic, cationic, nonionic or amphoteric group, preferably one of the groups preferred for X, or in the formulae (IIa), (IIb), (IIc) and (V) are also equal to H:

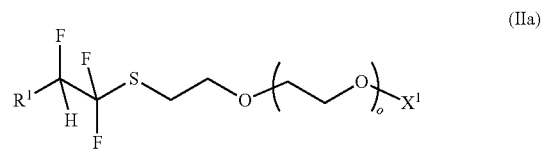

(IIa)

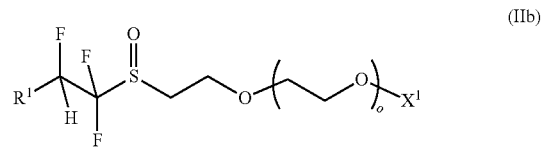

(IIb)

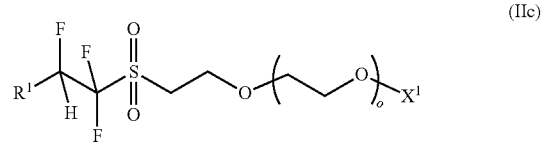

(IIc)

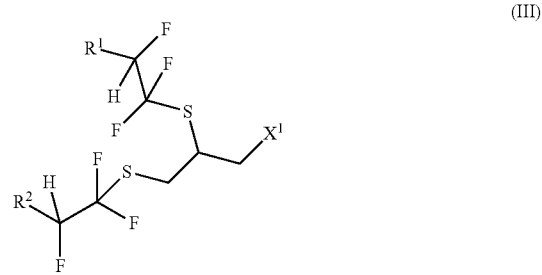

(III)

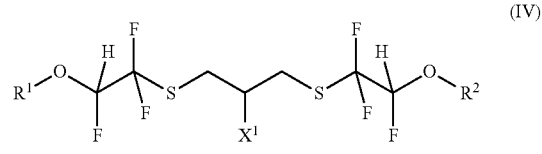

(IV)

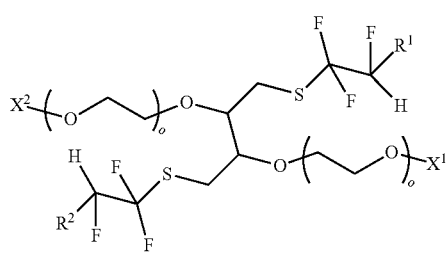

(V)

In a preferred variant of the compounds of the formulae (II) to (V), $X^1$ and $X^2$, independently of one another, are an anionic or nonionic group, in particular the groups preferred for X, and $R^1$ and $R^2$, independently of one another, are a $CF_3$—$(CF_2)_{1-2}$—O— group. $R^1$ and $R^2$, and $X^1$ and $X^2$ are preferably identical.

Particular preference is given to compounds which contain, as $X^1$ and/or $X^2$, the groups —$SO_3^-$, —$OSO_3^-$, —$COO^-$, —$PO_3^{2-}$, —$OP(O)(O^-)O$— or —$OPO_3^{2-}$, polyethylene glycol or polypropylene glycol, —CH(OH)—$CH_2$—NH-sach, —Y—($CH_2$—$CH_2$—O)$_v$—$R^4$, betaines, or sulfobetaines. Preferred counterions here are $H^+$, $Na^+$, $K^+$ and $NH_4^+$, in particular $Na^+$. Particular preference is given to: —$SO_3^-$, —$COO^-$, —$OP(O)(O^-)O$— or —$OPO_3^{2-}$, polyethylene glycol or polypropylene glycol, sulfobetaines, the group —CH(OH)—$CH_2$—NH-sach and the group —Y—($CH_2$—$CH_2$—O)$_v$—$R^4$. Sach here=various sugars and Y=S, O or NH, preferably O, $R^4$=H or alkyl, preferably H or $CH_3$, and v=1-100, preferably 1-30, in particular also 1-25. Compounds where X=—$SO_3^-$ may also be particularly advantageous. Compounds of the formulae (IIa) and (III) to (V), especially those having the preferred variables, are particularly preferred.

In another variant of the invention, the fluorinated compounds are preferably based on esters of maleic acid and aconitic acid. These compounds are represented by the formulae (VI) and (VII), where $L^1$, $L^2$ and $L^3$, independently of one another, are a saturated or unsaturated, branched or unbranched hydrocarbon unit, optionally containing heteroatoms, where no —O—O— bonds are present, in particular a linear or branched C1-C6-alkyl group, particularly preferably a C1-C4-alkyl group, X is a hydrophilic group and $R^1$, $R^2$ and $R^3$, independently of one another, are a fluorinated, linear or branched alkyl group, optionally containing heteroatoms:

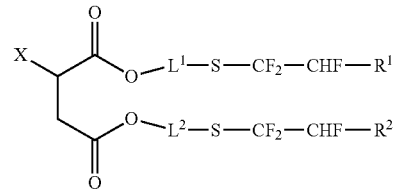

(VI)

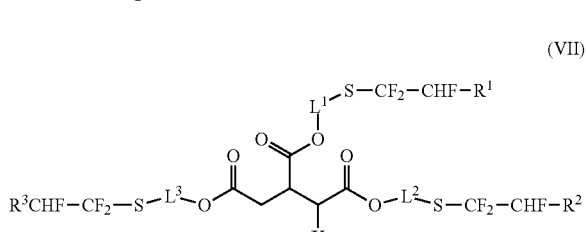

(VII)

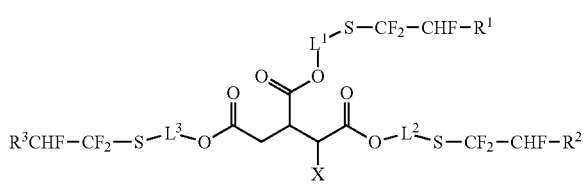

In a preferred variant of the compounds of the formulae (VI) and (VII), $L^1$, $L^2$ and $L^3$, independently of one another, are a linear or branched C1-C6-alkyl group, particularly preferably a C1-C4-alkyl group, X is an anionic or nonionic group and $R^1$, $R^2$ and $R^3$, independently of one another, are a $CF_3$—$(CF_2)_{1-2}$—O-group. Preferably, $L^1$, $L^2$ and $L^3$ are identical and $R^1$, $R^2$ and $R^3$ are identical.

Compounds of the formulae (I) to (VII) in which one or more of the variables have the preferred meanings are particularly advantageous. Compounds of the formulae (I) to (VII) in which all said variables have the preferred meanings, in particular the particularly preferred meanings, are particularly advantageous.

Particular preference is given to compounds of the formulae (VIII) to (XVIII) in which the variables have the meanings indicated for the formulae (I) to (VII), in particular the preferred meanings, and PEG stands for polyethylene glycol, polypropylene glycol, polyethylene glycol alkyl ether or polypropylene glycol alkyl ether and $R^a$, $R^b$ and $R^c$=H or C1-4-alkyl, in particular H or $CH_3$. Alkyl ethers are preferably C1-C4-alkyl ethers, in particular C1-C2-alkyl ethers, especially methyl ethers:

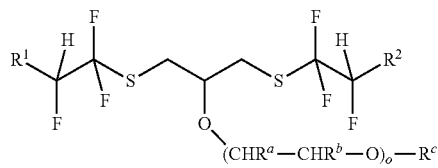

(VIII)

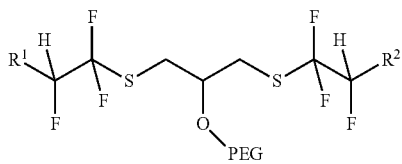

(IX)

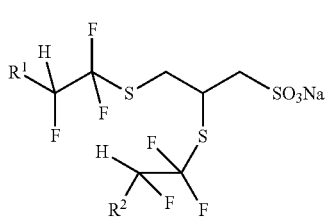

(X)                                    (X')

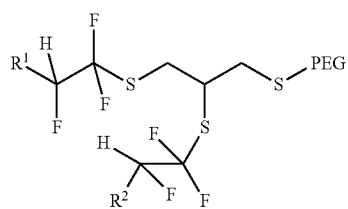
(XI)

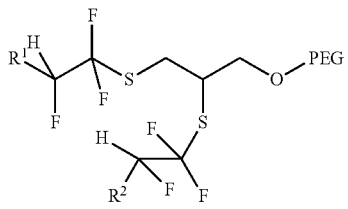
(XII)

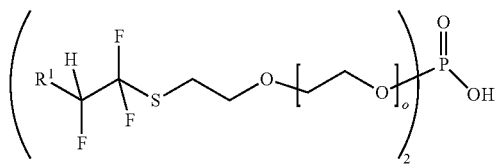
(XIII)    (XIII')

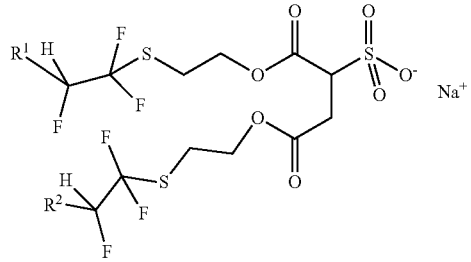
(XIV)    (XIVa)

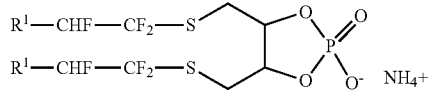
(XV)    (XVI)

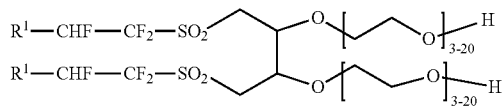
(XVIa)    (XVII)

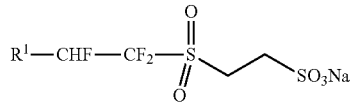
(XVIIa)

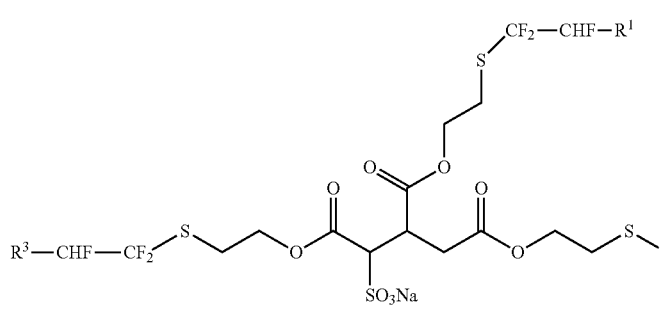
(XVIII)

Particular preference is given to compounds of the formulae (VIII) to (XVIII) in which the fluorinated groups $R^1$ and $R^2$ or $R^1$, $R^2$ and $R^3$ are selected, independently of one another, from the groups: $CF_3—(CF_2)_{0-3}—$, $CF_3—(CF_2)_{0-3}—O—$, $CF_3—(CF_2)_{0-3}—O—(CF_2)_{1-3}—$, $CF_3—(CF_2)_{0-3}—O—(CF_2)_{1-3}—O—$, $CF_3—(CF_2)_{0-3}—O—(CF_2)_{1-3}—O—CF_2—$, $CF_3—(CF_2)_{0-3}O—(CF_2—O)_{1-8}—$ and $CF_3—(CF_2)_{0-3}—O—(CF_2—O)_{1-8}—CF_2—$.

The fluorinated groups $R^1$ and $R^2$ or $R^1$, $R^2$ and $R^3$ are especially preferably, independently of one another, a $CF_3—(CF_2)_{1-2}—O$ group, in particular a $CF_3—CF_2—CF_2—O$ group. Particularly preferably, $R^1$ and $R^2$ are identical and $R^1$, $R^2$ and $R^3$ are identical. o is preferably equal to 1-30, in particular 3, 5, 6, 10, 12, 15, 18, 20 or 24, in particular 3, 10 or 18. Compounds of the formulae (VIII) to (XIV) and (XV), (XVI), (XVII) and (XVIII), especially those having the preferred variables, are especially preferred.

In particular, the following compounds of the formulae (XIX) to (XXIV), where o=0, 10 or 18 and R=methyl or ethyl, are particularly preferred:

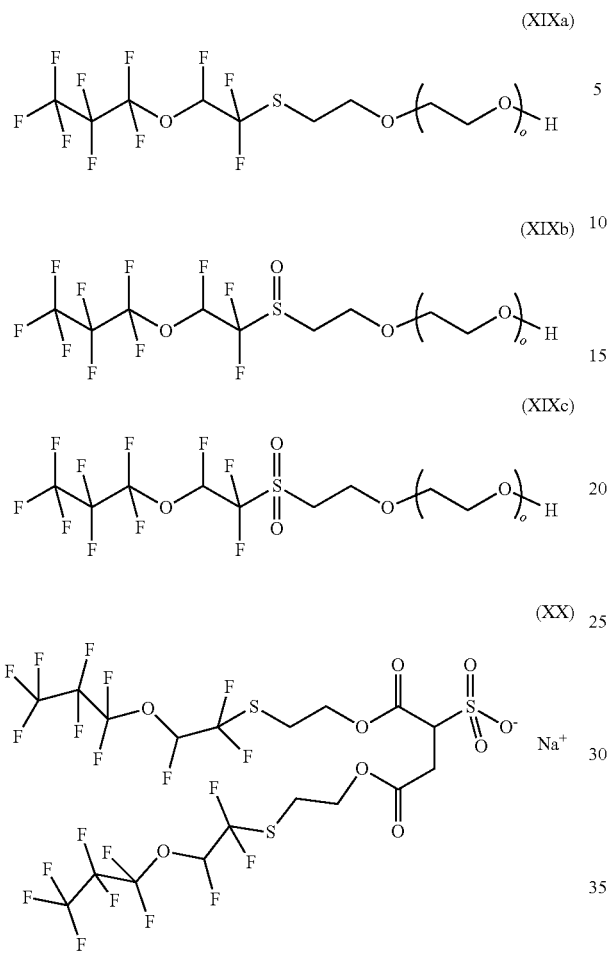
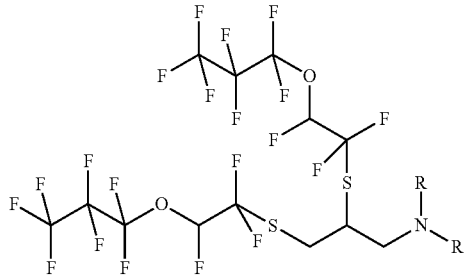
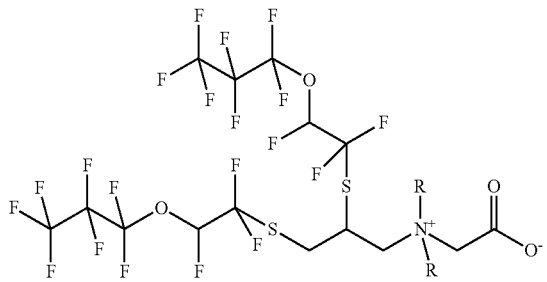
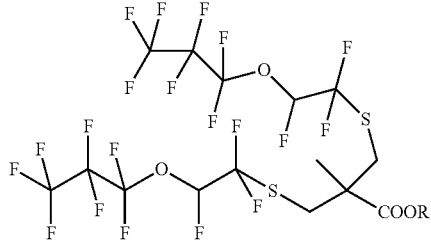
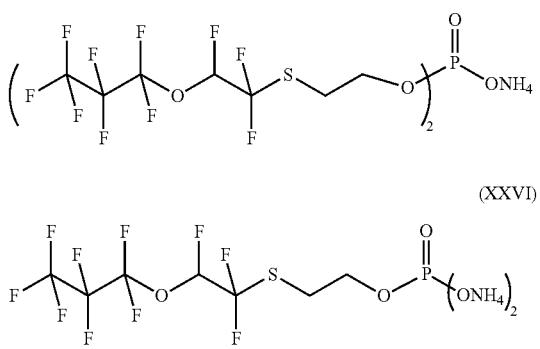
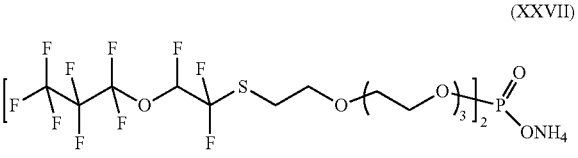
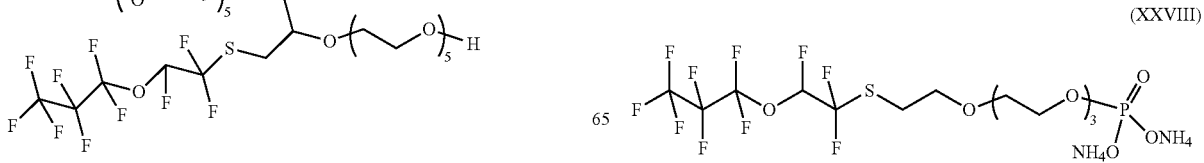

(XXIX)

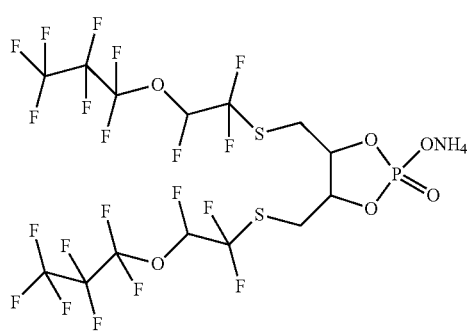

Compounds of the formulae (XIXa) and (XX) to (XXIX), especially those having the preferred variables, are particularly preferred.

The fluorosurfactants according to the invention based on perfluoroolefins have lower stability than conventional fluorosurfactants and can therefore be degraded more easily by physical/chemical processes, and are preferably not persistent. The fluorosurfactants according to the invention may be distinguished by very efficient reduction of the surface tension energy in aqueous solutions. In addition, these compounds preferably have a low CMC and a low foaming behaviour.

Furthermore, the introduction of the sulfide bridge enables a broadening of the variation of the molecule structure. As is known, sulfides can be converted into sulfoxides using methods which are known to the person skilled in the art from the literature, which allows additional "trimming" of the molecule polarity with respect to hydrophilicity.

The compounds according to the invention can be prepared by processes known to the person skilled in the art. With the aid of perfluoroolefins and heterofunctional molecules, the novel fluorosurfactants, which are able to combine a number of positive effects, can be prepared specifically. It has been found that thiol compounds have significantly higher reactivity than comparable alcohols owing to their increased nucleophilicity. This advantage can now be utilised by etherification of mono- or polyfunctional alcohols which additionally also contain one or more thiol groups selectively on the sulfur group without the introduction of a protecting group. The free OH groups can then be reacted further in a second step. This property results in it being possible greatly to simplify the performance of the synthesis compared with the corresponding alcohol compounds and in the yield being increased.

Schemes 1 to 6 below show illustrative syntheses of compounds according to the invention. These processes are generally known to the person skilled in the art and can be carried out under conventional conditions. Use can preferably be made of the following perfluoroolefin compounds, which are mentioned by way of example:

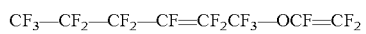

The compounds according to the invention, in particular compounds of the formulae (II) to (VII), can preferably be prepared by the following synthetic routes (shown by way of example for compounds where $R^1$=$CF_3CF_2CF_2O$—).

Scheme 1

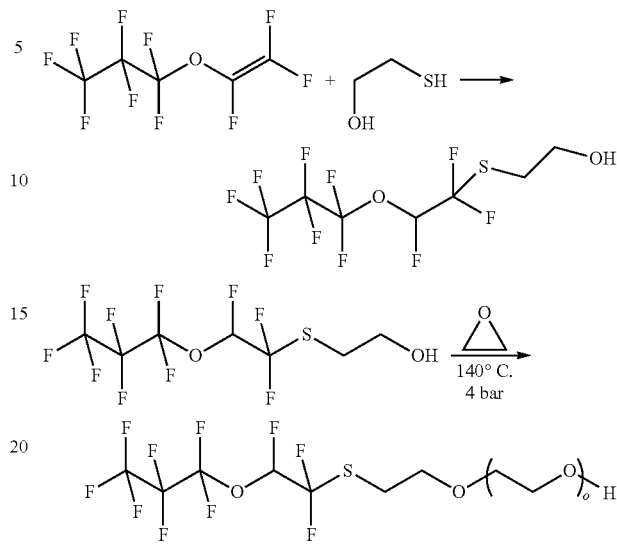

Scheme 1a

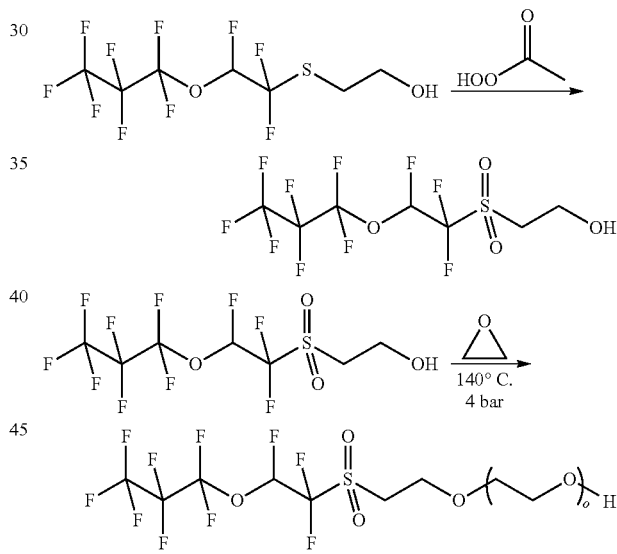

Scheme 2

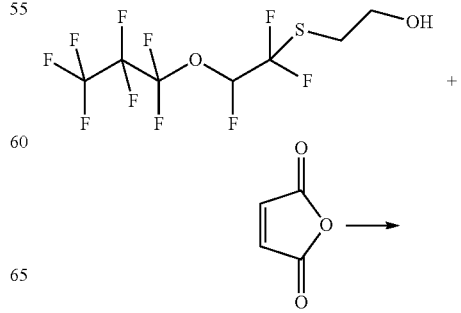

15
-continued
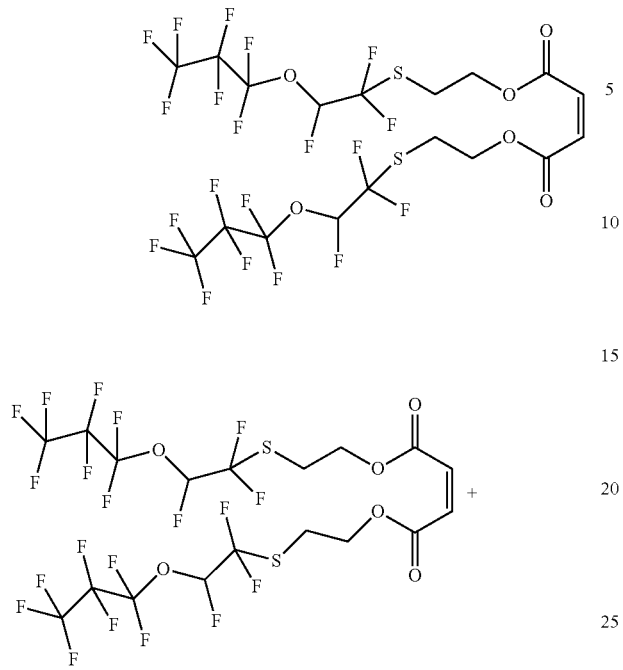
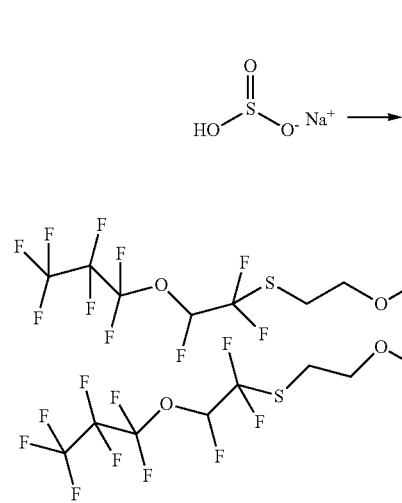
Scheme 2a
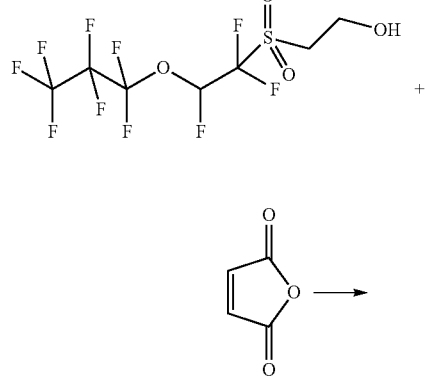
16
-continued
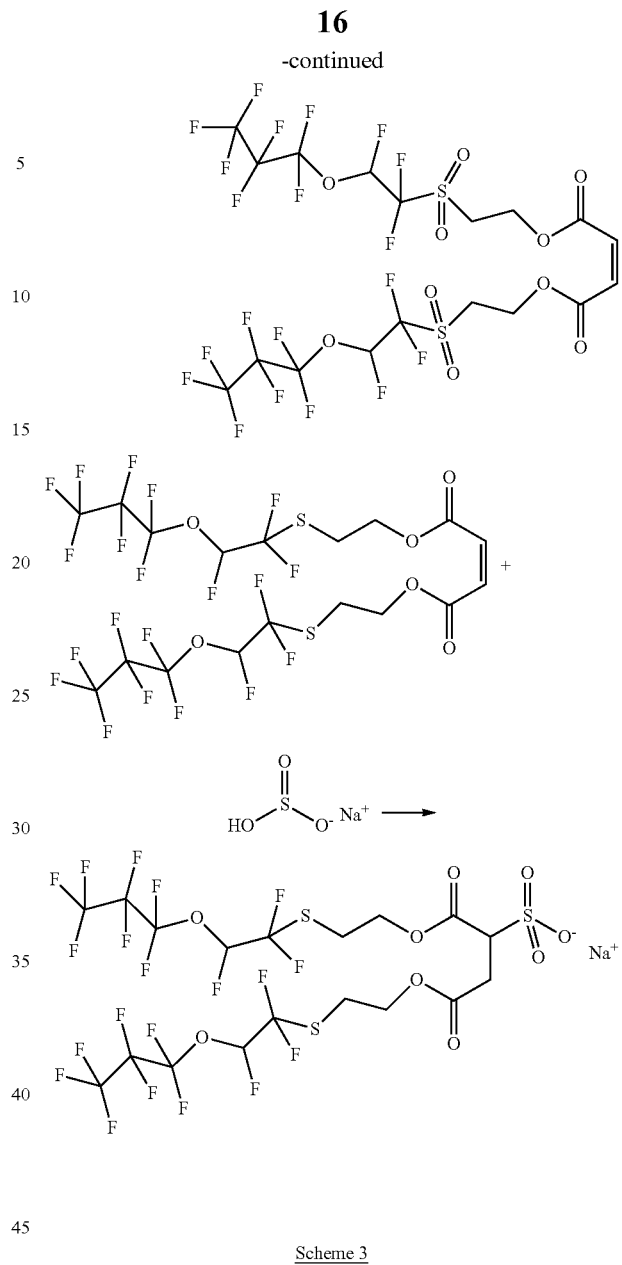
Scheme 3
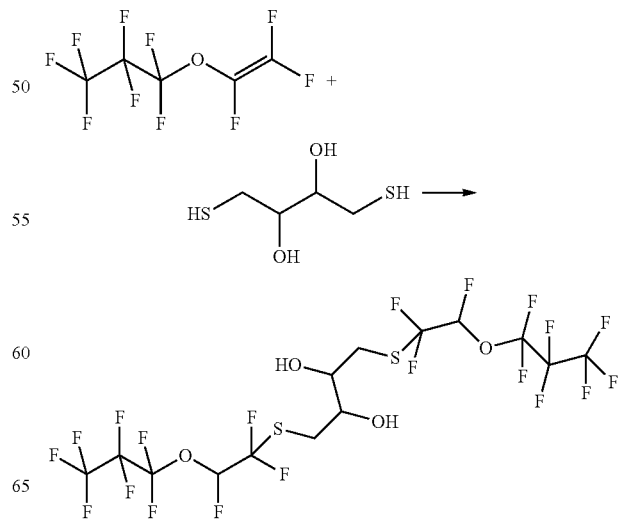

-continued

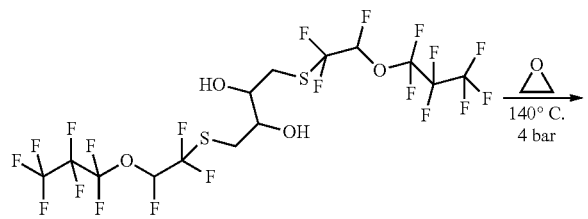

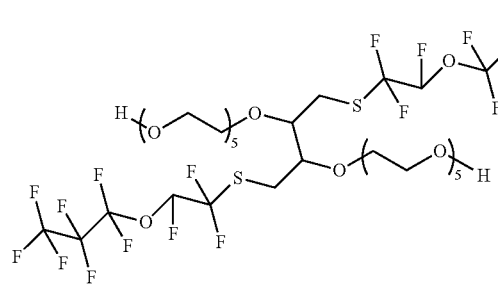

Scheme 4

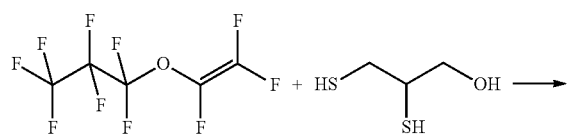

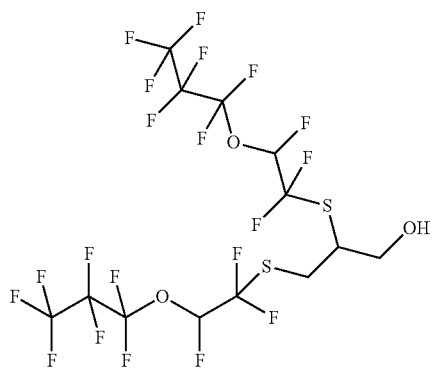

Scheme 5

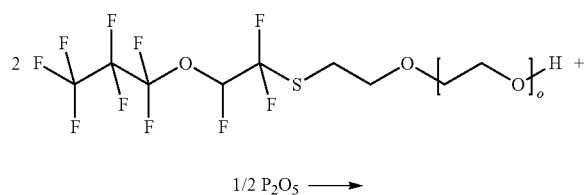

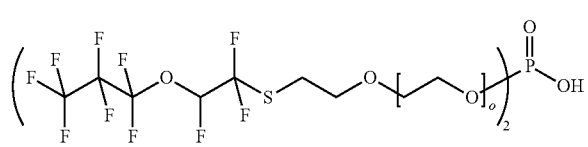

Scheme 5a

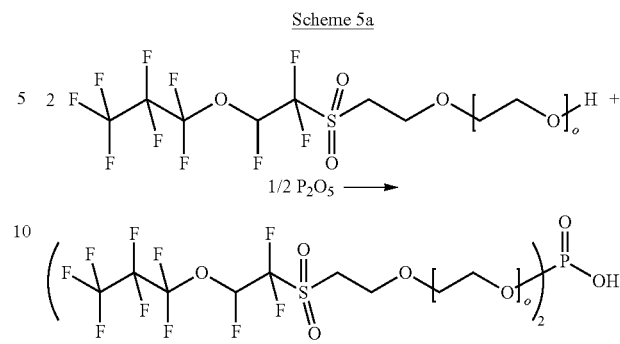

Scheme 6

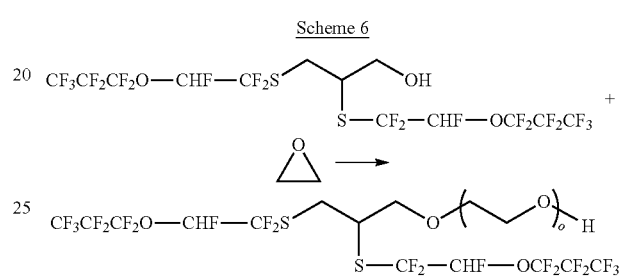

Further compounds according to the invention can be prepared analogously to the illustrative reactions shown above or by other methods known per se to the person skilled in the art from the literature. Particular preference is given here to compounds of the formulae (VIII) to (XXIV). These processes are generally known to the person skilled in the art and can be carried out under conventional conditions. The starting compounds used are commercially available and/or their preparation is familiar to the person skilled in the art.

Advantages of the compounds according to the invention may be, in particular:
  a surface activity which is equal or superior to that of conventional hydrocarbon surfactants with respect to efficiency and/or effectiveness,
  biological and/or abiotic degradability of the substances without the formation of persistent perfluorinated degradation products, such as PFOA (perfluorooctanoic acid) or PFOS (perfluorooctanesulfonate),
  can be prepared by simple processes,
  weak foaming action and/or low foam stabilisation,
  good processability in formulations and/or
  storage stability.

The compounds according to the invention can preferably have particular surface activity. The compounds of the formula (I) according to the invention, in particular the compounds of the formulae (II) and (VII) and preferably of the formulae (VIII) to (XXIV), may in addition have improved environmental properties since they do not degrade chemically or biologically to give long-chain PFCAs or PFASs. The compounds according to the invention can preferably be converted completely into mineralisable/regeneratable compounds by corresponding environmental influences.

A process for the degradation of the fluorine-containing compounds comprises the following steps:
  a) biological and/or abiotic degradation of the carbon skeleton of the fluorine-containing compounds with formation of, preferably non-toxic, fluorine-containing compounds having a sufficiently high vapour pressure, b) conversion of the fluorine-containing compounds having a high vapour pressure formed in step a) into a gas phase, c) degradation of the fluorine-containing compounds having a high vapour pressure formed in step a) to give low-molecular-weight compounds by UV irradiation in the gas phase, d) conversion of the low-molecular-weight compounds formed in step c) from the gas phase into a liquid and/or solid phase, e) mineralisation of the low-molecular-weight compounds of the liquid and/or solid phase formed in step c).

Preferably, no fluorine-containing salts are formed in step a).

In particular, no perfluorinated compounds are formed in step a).

The compounds of the formulae (I) to (XXIV) can preferably be used as surface-active agents, preferably as surfactant, hydrophobicisation agent, interface promoter, viscosity reducer, foam stabiliser or emulsifier. The present invention furthermore relates to the use of the compounds according to the invention and the preferred embodiments described above as surface-active agents, for example for improving the flow behaviour and the wetting capacity of coating formulations. Use is preferably made of fluorosurfactants of the formulae (I) to (VII), in particular of the formulae (VIII) to (XXIV), in particular the particularly preferred compounds mentioned.

Besides the compounds of the formula (I), in particular the preferred compounds of the formulae (II) to (VII), especially of the formulae (VIII) to (XXIV), the mixtures according to the invention may also comprise solvents, additives, assistants and fillers as well as non-fluorinated surfactants. Mention may be made by way of example of silicone particles, plasticisers and surface-modified pigments.

Preferred areas of use are, for example, the use of the fluorosurfactants of the formula (I) according to the invention and the preferred compounds as additives in preparations for surface coating, such as paints, coatings, protective coatings, special coatings in electronic or semiconductor applications (for example photoresists, top antireflective coatings, bottom antireflective coatings) or in optical applications (for example photographic coatings, coatings of optical elements), in agrochemicals, in polishes and waxes, for example for furniture, flooring and automobiles, in particular in floor polishes, in fire-extinguishing compositions, lubricants, in photolithographic processes, in particular in immersion photolithography processes, for example in developer solutions, rinse solutions, immersion oils and/or in the photoresists themselves, especially for the production of printed circuits or in additive preparations for addition to corresponding preparations. In addition, the compounds which can be used in accordance with the invention as surfactant are suitable for washing and cleaning applications, and for use as additives/surfactants in cosmetic products, such as, for example, hair- and body-care products (for example shampoos, hair rinses and hair conditioners), foam baths, creams or lotions having one or more of the following functions: emulsifiers, wetting agents, foaming agents, glidants, antistatic, agents for increasing the resistance to skin greases. For use, the fluorosurfactants according to the invention are usually introduced into correspondingly designed preparations. Usual use concentrations are 0.01-1.0% by weight of the surfactants according to the invention, based on the entire preparation.

The present invention likewise relates to corresponding compositions comprising the fluorosurfactants according to the invention. Such compositions preferably comprise a vehicle which is suitable for the respective intended use, and optionally further active substances and/or optionally assistants. Preferred compositions are paint and coating preparations, fire-extinguishing compositions, lubricants, washing and cleaning compositions and deicers or developer solutions, rinse solutions, immersion oils and photoresists for photolithographic processes, in particular for immersion photolithography processes and in particular for the production of printed circuits, agrochemicals, floor polishes, cosmetic products or hydrophobicising compositions for textile finishing or glass treatment. Preferred compositions here are paint and coating preparations and printing inks.

In addition, the present invention also relates to water-based coating formulations which comprise the fluorosurfactants according to the invention, alone or in a mixture with additives. Coating formulations based on the following synthetic film formers are preferably used: polycondensation resins, such as alkyd resins, saturated/unsaturated polyesters, polyamides/imides, silicone resins; phenolic resins; urea resins and melamine resins, polyaddition resins, such as polyurethanes and epoxy resins, polymerisation resins, such as polyolefins, polyvinyl compounds and polyacrylates.

In addition, the fluorosurfactants according to the invention are also suitable for use in coatings based on natural products and modified natural products. Preference is given to coatings based on oils, polysaccharides, such as starch and cellulose, and also based on natural resins, such as cyclic oligoterpenes, polyterpenes and/or shellac.

The fluorosurfactants according to the invention can be used both in physically curing (thermoplastics) coating systems and also in crosslinking (elastomers and thermosets) water-borne coating systems. The fluorosurfactants according to the invention preferably improve the flow and wetting properties of the coating systems.

The present invention relates to all uses mentioned here of fluorosurfactants to be employed in accordance with the invention, in particular of the preferred compounds. The respective use of fluorosurfactants for the said purposes is known to the person skilled in the art, meaning that the use of the fluorosurfactants to be employed in accordance with the invention presents no problems.

The following examples explain the present invention in greater detail without restricting the scope of protection.

EXAMPLES

The NMR spectra are measured using a Bruker 400 MHz spectrometer with internal standard.

The IR spectra are measured using a Brucker Alpha Platinum-ATR spectrometer.

Determination of the Static Surface Tension

The static surface tensions $\gamma$ of aqueous surfactant solutions having various concentrations c (grams per litre) are determined.

Instrument: Dataphysics tensiometer (model DCAT 11)

Temperature of the measurement solutions: 20°±0.2° C.

Measurement method employed: measurement of the surface tension using the Wilhelmy plate method in accordance with DIN EN 14370.

Plate: platinum, length=19.9 mm

In the plate method, the surface or interfacial tension of the surfactant solution is calculated from the force acting on the wetted length of a plate, in accordance with the following formula:

$$\gamma = \frac{F}{L \cdot \cos\theta} = \frac{F}{L}$$

γ=interfacial or surface tension; F=force acting on the balance; L=wetted length (19.9 mm); θ=contact angle. The plate consists of roughened platinum and is thus optimally wetted so that the contact angle θ is close to 0°.

The term cos θ therefore approximately reaches the value 1, so that only the measured force and the length of the plate have to be taken into account.

Abbreviations

EO ethylene oxide units
THF tetrahydrofuran
MTBE tert-butyl methyl ether
b.p. boiling point
w % percent by weight Example 1: Synthesis of Compounds of the Formula (XIX)

Example 1a

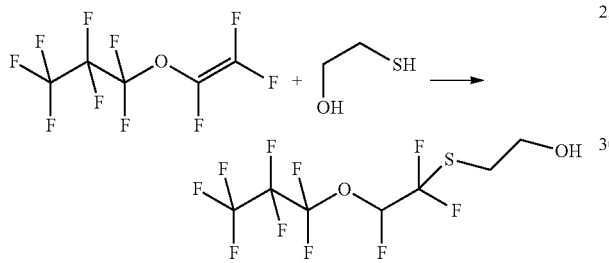

77.3 g of 1,1,1,2,2,3,3-heptafluoro-3-trifluorovinyloxy-propane, 52.2 g of 2-mercaptoethanol, 12.05 g of potassium carbonate and 50 ml of acetonitrile are combined in a pressure reactor. The reaction mixture is stirred at 100° C. for 20 h. 50 ml of water and 50 ml of MTBE are added to the reaction mixture, and the phases are separated. The aqueous phase is extracted with 2×30 ml of MTBE. The combined organic phases are subsequently washed with 40 ml of water and 40 ml of saturated NaCl solution. The extract is dried over sodium sulfate, and the solvent is distilled off. The residue is then subjected to fractional vacuum distillation.

The product here has a head temperature of 49° C. at a pressure of 0.058 mbar. Product weight: 63.47 g 1H-NMR: 7.2 ppm (dt, 1 H, —CFH); 5.1 ppm (t, 1 H, —OH);
3.6 ppm (q, 2 H, —CH2-OH); 3.0 ppm (t, 2 H, S—CH2—CH2)

Example 1b

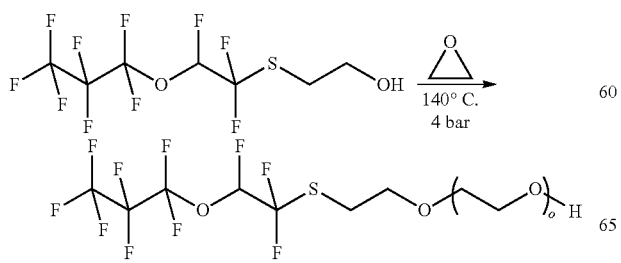

The alcohol prepared in Example 1a is reacted with ethylene oxide at 140° C. and max. 4 bar in a pressure reactor to give the corresponding fluorosurfactants. Various chain lengths can be achieved depending on the reaction time. The materials synthesised here have a statistical EO chain length of 3, 10 or 18 units.

Example 1c: n=3

1H-NMR: 7.2 ppm (dt, 1 H, —CFH); 3.6 ppm (q, 2 H, —CH2-OH); 3.55-3.40 (m, 12 H, —CH2CH2-O); 3.0 ppm (t, 2 H, S—CH2-CH2)

Example 1d: n=10

1H-NMR: 7.2 ppm (dt, 1 H, —CFH); 3.6 ppm (q, 2 H, —CH2-OH); 3.55-3.40 (m, 42 H, —CH2CH2-O); 3.0 ppm (t, 2 H, S—CH2-CH2)

Example 1e: n=18

1H-NMR: 7.2 ppm (dt, 1 H, —CFH); 3.6 ppm (q, 2 H, —CH2-OH); 3.55-3.40 (m, 74 H, —CH2CH2-O); 3.0 ppm (t, 2 H, S—CH2-CH2)

Example 1f

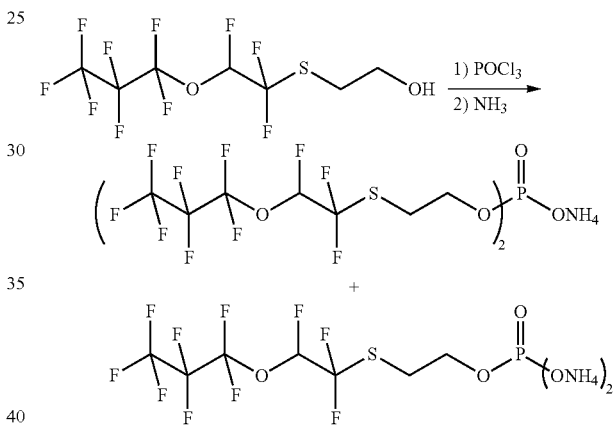

11 g of the alcohol from Example 1a are initially introduced in 4 ml of toluene in a reaction flask and heated to 60° C. 2.00 g of phosphoryl chloride are slowly added over the course of 10 min. The reaction mixture is subsequently heated to 115° C. and stirred at this temperature for 5.5 h. The batch is subsequently cooled to 90° C. and carefully hydrolysed using 0.3 ml of water, and the mixture is stirred at this temperature for a further hour. The solvent is subsequently removed, leaving a brown residue.

20 ml of MTBE and 20 ml of water are added to the crude product, and the phases are separated. The aqueous phase is extracted with 2×30 ml of MTBE. The combined organic phases are subsequently neutralised using ammonia solution and separated off.

Product weight: 11.18 g.

1H-NMR: 7.3-7.1 ppm (m, 2 H, —CFH); 4.0-3.2 ppm (m, S—CH2-CH2); 31 P-NMR: −0.7 ppm (t, 2 P); −1.8 ppm (quin, 1 P), i.e. mono- and diester are present in the ratio 2/1.

Example 1 g

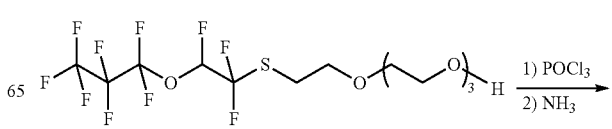

-continued

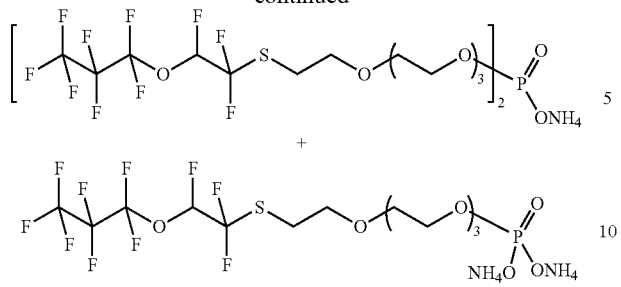

11 g of the alcohol from Example 1c are reacted with 1.5 g of POCl₃ analogously to Example 1f.
Yield 11.0 g
1H-NMR: 7.3-7.1 ppm (m, 2H, —CFH); 3.8-3.3 ppm (m, 4H, S—CH2-CH2) and (m, 24H, CH2-CH2-O);
31 P-NMR: −0.7 ppm (t, 3 P); −1.8 ppm (quin, 2 P), i.e. mono- and diester are present in the ratio 2/1.

Example 1h

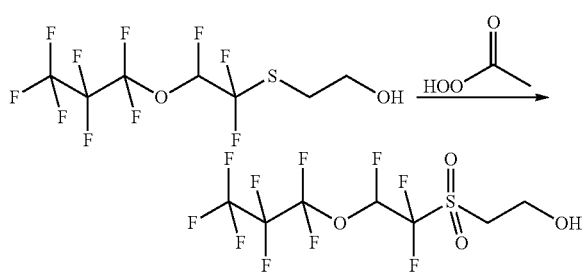

6.5 g of the alcohol prepared in Example 1a are initially introduced in 24 ml of acetonitrile in a round-bottomed flask, and 5.4 ml of 40% peracetic acid are slowly added dropwise with stirring. The reaction mixture is then heated to 80° C. and stirred at this temperature for 24 h. 30 ml of water and 30 ml of MTBE are added to the reaction mixture, and the phases are separated. The aqueous phase is extracted with 2×30 ml of MTBE. The combined organic phases are subsequently washed with 40 ml of water and 40 ml of saturated NaCl solution. The extract is dried over sodium sulfate, and the solvent is distilled off. Product weight: 6.69 g
1H-NMR: 8.2 and 7.2 ppm (m, 1 H, —CFH); 4.0 ppm (m, 4 H, SO2-CH2-CH2-OH)

Example 2: Synthesis of the Compound of the Formula (XX)

Example 2a: Preparation of the Fluorinated Maleic Acid Ester

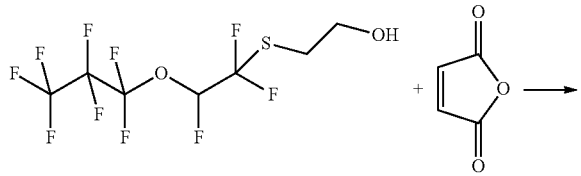

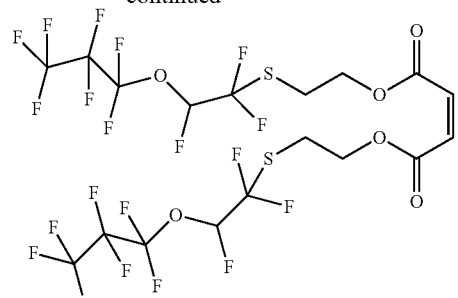

10.49 g of the alcohol prepared in Example 1a, 1.30 g of maleic anhydride and 0.68 g of p-toluenesulfonic acid monohydrate are combined in 30 ml of toluene in a round-bottomed flask. The reaction mixture is stirred under reflux on a water separator for 24 h. 30 ml of water and 30 ml of MTBE are added to the reaction mixture, and the phases are separated. The aqueous phase is extracted twice with 20 ml of MTBE. The combined organic phases are subsequently washed with 30 ml of water and 30 ml of saturated NaCl solution. The extract is dried over sodium sulfate, and the solvent is distilled off. Product weight: 10.68 g
1H-NMR: 7.2 ppm (dt, 2 H, —CFH); 6.5 ppm (m, 2 H, —CH=CH—);
4.3 ppm (t, 2 H, —CH2-CH2-O); 3.2 ppm (t, 2 H, —CH2-CH2-S—)

Example 2b: Preparation of the Fluorinated Sulfosuccinate

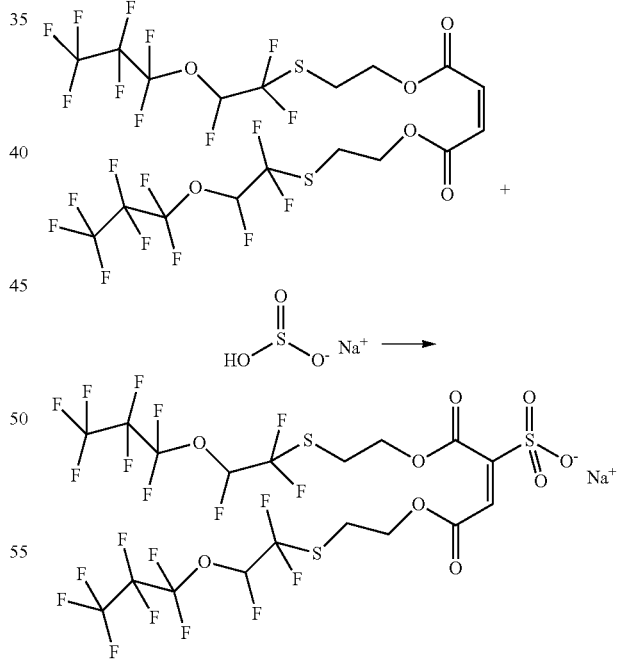

10.00 g of the fluorine-containing maleic acid ester, 2.71 g of a 39% sodium hydrogensulfite solution and 30 ml of 2-propanol are initially introduced in a round-bottomed flask. The pH of the reaction mixture is then adjusted to pH 6.3 using sodium hydroxide solution. The reaction mixture is subsequently stirred at 95° C. for 96 h. 30 ml of MTBE and 30 ml of water are added to the reaction mixture, and the phases are separated. The aqueous phase is extracted twice with 20 ml of MTBE. The combined organic phases are subsequently washed with 30 ml of water and 30 ml of saturated NaCl solution.

The extract is dried over sodium sulfate, and the solvent is distilled off.

Yield: 6.64 g

1H-NMR: 7.2 ppm (dt, 2 H, —CFH); 4.2 ppm (m, 4 H, S—CH2-CH2);

3.7 ppm (dd, 1 H, —CH—SO3-); 3.2 ppm (t, 4 H, CH2-CH2-O);

2.8-3.0 ppm (m, 2 H, —CH2-CH);

Example 2c: Precursor for the Synthesis of the Compound of the Formula (XVIII)

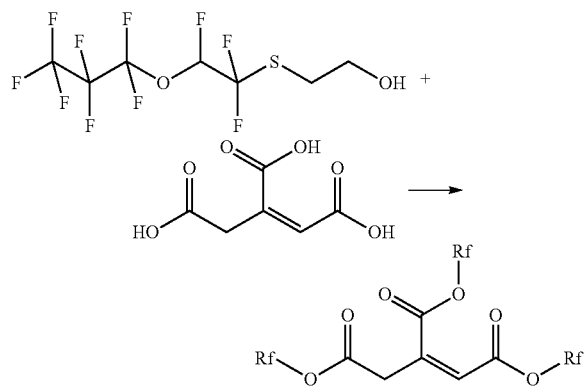

9.49 g of the alcohol prepared in Example 1a, 1.50 g of aconitic acid and 0.45 g of p-toluenesulfonic acid monohydrate are combined in 50 ml of toluene in a round-bottomed flask. The reaction mixture is stirred at 115° C. on a water separator for 72 h. 30 ml of water and 30 ml of MTBE are added to the reaction mixture, and the phases are separated. The aqueous phase is extracted twice with 20 ml of MTBE. The combined organic phases are subsequently washed with 30 ml of water and 30 ml of saturated NaCl solution. The extract is dried over sodium sulfate, and the solvent is removed. Product weight: 6.78 g 1H-NMR: 7.8-7.6 ppm (m, 2 H, —CFH); 6.8 ppm (s, H, —C═CH—); 4.4-4.0 ppm (t, 2 H, —CH2-CH2-S—); 3.7 ppm (s, H, CH2-C═CH—); 3.2-2.8 ppm (t, 2 H, —CH2-CH2-O)

Example 2d: Synthesis of the Compound of the Formula (XVIII)

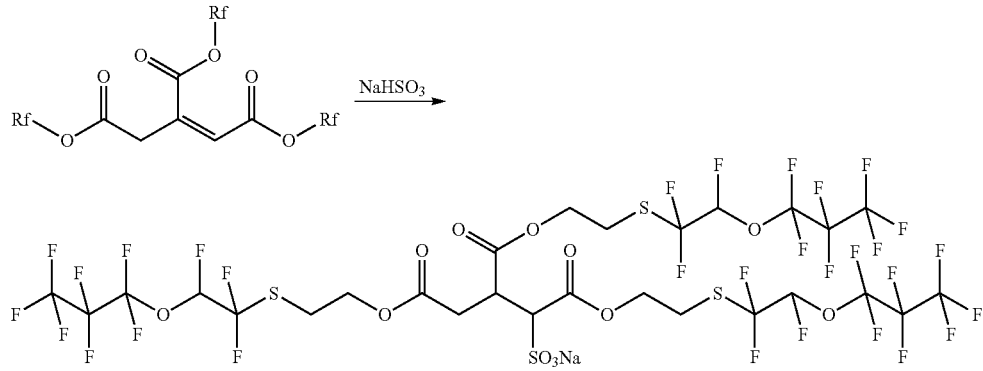

6.78 g of the fluorine-containing aconitic acid ester from Example 2c, 1.22 g of a 39% sodium hydrogensulfite solution and 24 ml of 2-propanol are initially introduced in a round-bottomed flask. The pH of the reaction mixture is then adjusted to pH 6.3 using sodium hydroxide solution. The reaction mixture is subsequently stirred at 95° C. for 96 h. 30 ml of MTBE and 30 ml of water are added to the reaction mixture, and the phases are separated. The aqueous phase is extracted twice with 20 ml of MTBE. The combined organic phases are subsequently washed with 30 ml of water and 30 ml of saturated NaCl solution. The extract is dried over sodium sulfate, and the solvent is removed. Yield: 6.26 g 1H-NMR: 7.0 ppm (dt, 3 H, —CFH); 4.2-3.8 ppm (m, 6 H, S—CH2-CH2); 3.5-2.5 ppm (m, 10 H, CH2-CH2-O) and CH2-RCH—CH—SO3H Example 3: Synthesis of the Compound of the Formula (XXI) where n=5; 7.510

Example 3a: Preparation of the Fluorinated Diol

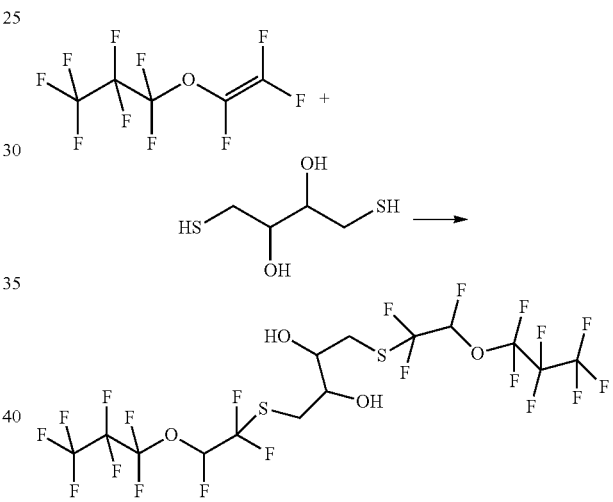

8.63 g of 1,1,1,2,2,3,3-heptafluoro-3-trifluorovinyloxy-propane, 2.50 g of 1,4-dimercaptobutane-2,3-diol, 0.67 g of potassium carbonate and 30 ml of acetonitrile are combined in a pressure reactor and stirred at 120° C. for 20 h. 30 ml of water and 30 ml of MTBE are added to the reaction mixture, and the phases are separated. The aqueous phase is extracted twice with 20 ml of MTBE. The combined organic phases are subsequently washed with 30 ml of water and 30 ml of saturated NaCl solution. The extract is then dried over sodium sulfate, and the solvent is distilled off. Product weight: 9.82 g 1H-NMR: 7.2 ppm (dt, 2H, —CFH); 5.3 ppm (m, 2 H, —OH);

3.7 ppm (dt, 2 H, CH2-CH—O—); 2.9-3.2 ppm (m, 4 H, CH2-S);

Example 3b: Preparation of the Ethoxylated Compound

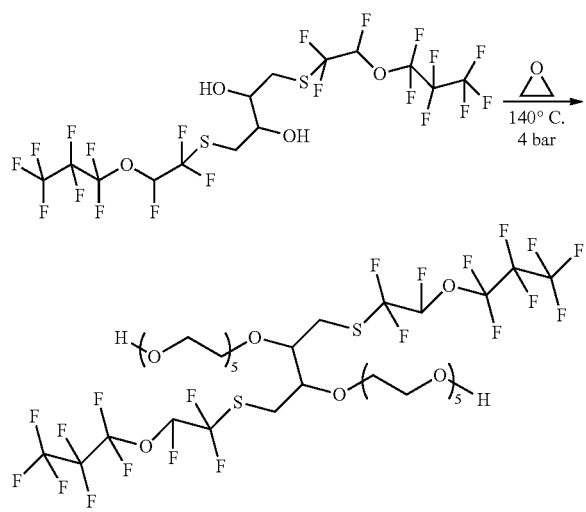

The alcohol prepared is reacted with ethylene oxide at 140° C. and max. 4 bar in a pressure reactor to give the corresponding fluorosurfactant. Various chain lengths can be achieved depending on the reaction time. The material synthesised here has a statistical EO chain length of 5 units.

1H-NMR: 7.2 ppm (dt, 2 H, —CFH); 3.85-3.4 ppm (m, 44 H); 2.9-3.2 ppm (m, 4 H, CH2-S);

Examples 3c-e

Carried out analogously to Example 3b, only with the ethoxylation being carried out longer until an average recurring number of 3c: EO=10; 3d: EO=15; 3e EO=20 has been reached.

Example 3f

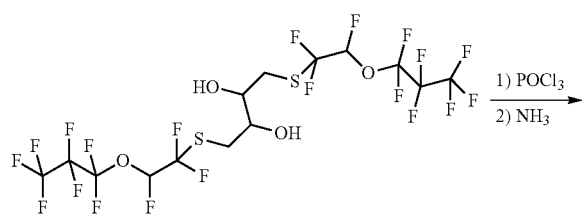

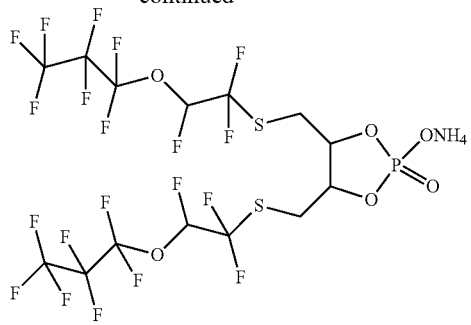

11 g of the compound from Example 3a are initially introduced in 4 ml of toluene in a reaction flask and heated to 60° C. 1.98 g of phosphoryl chloride are slowly added over the course of 10 min. The reaction mixture is subsequently heated to 115° C. and stirred at this temperature for 18 h. The batch is subsequently cooled to 90° C. and carefully hydrolysed using 0.3 ml of water, and the mixture is stirred at this temperature for a further hour. The solvent is subsequently removed, leaving a brown residue.

20 ml of MTBE and 20 ml of water are added to the crude product, and the phases are separated. The aqueous phase is extracted with 2×30 ml of MTBE. The combined organic phases are subsequently neutralised using ammonia solution and separated off.

Product weight: 11.18 g

1H-NMR: 7.2 ppm (dt, 2 H, —CFH); 3.75 ppm (m, 2 H, ROCH—CHOR); 2.75 ppm (m, 4 H, S—$CH_2$—CHR)

Example 4: Synthesis of Compounds of the Formula (XVII)

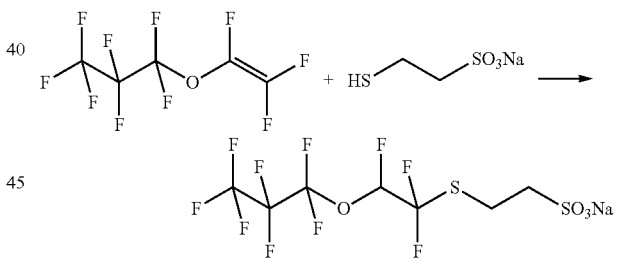

7.53 g of 1,1,1,2,2,3,3-heptafluoro-3-trifluorovinyloxy-propane, 3.58 g of the sodium salt of 2-mercaptoethane-sulfonic acid, 0.90 g of potassium carbonate and 30 ml of acetonitrile are combined in a pressure reactor and stirred at 110° C. for 18 h.

MTBE and water are added to the reaction mixture, and the phases are separated. The aqueous phase is extracted with 2×25 ml of MTBE, and the combined organic phases are washed with 30 ml of water and 30 ml of saturated NaCl solution.

The extract is dried over sodium sulfate, and the solvent is removed.

Product weight: 6.53 g

1H-NMR: 7.2 ppm (dt, 1 H, —CFH); 3.2-2.7 ppm (m, 4 H, S—$CH_2$—$CH_2$—$SO_3Na$);

Table 1 shows the static surface tension and the CMC (critical micelle concentration) of compounds according to the invention.

TABLE 1

Static surface tension measurement of the surfactants described above as 0.1% aqueous solution in dynes (mN/m)

| Ex. | 1c | 1d | 1e | 1f | 1g | 2b | 2d |
|---|---|---|---|---|---|---|---|
| Dynes | 20.4 | 20.5 | 27.0 | 20.0 | 17.0 | 16.0 | 20.2 |
| Ex. | 3b | 3c | 3d | 3e | 3f | 4 | |
| Dynes | 18.2 | 18.9 | 20.3 | 21.1 | 18.5 | 19.3 (1%) | |

The invention claimed is:

1. A compound of formula

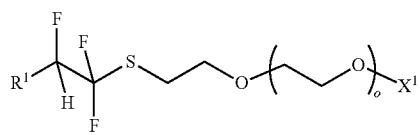
(IIa)

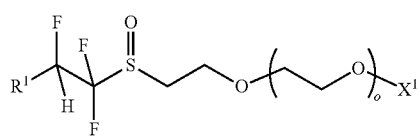
(IIb)

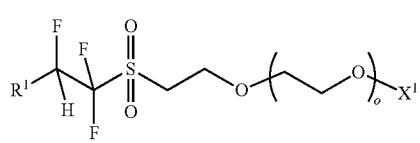
(IIc)

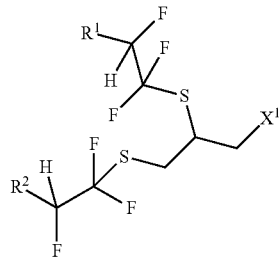
(III)

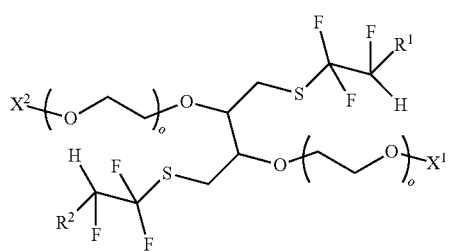
(V)

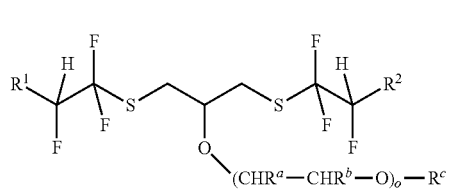
(VIII)

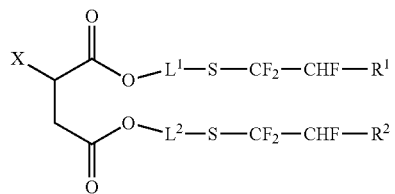
(VI)

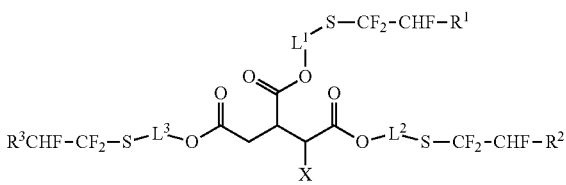
(VII)

where $R^1$, $R^2$ and $R^3$, independently of one another, $CF_3$—$(CF_2)_{1-2}$—O—, o=1-30, X=—$S_3^-$, —$OSO_3^-$, —$COO^-$, —$PO_3^{2-}$, —OP(O)(O$^-$)O—, —$OPO_3^{2-}$, a polyethylene glycol, a poly-propylene glycol, —CH(OH)—$CH_2$—NH-sach, —Y'—($CH_2$—$CH_2$—O)$_v$-$R^4$, a betaine, or a sulfobetaine, with counterions being H$^+$, Na$^+$, K$^+$ or NH$_4^+$, sach being a sugar, $X^1$ and $X^2$, independently of one another, have the meaning of X, or, in the formulae (IIa), (IIb), (IIc) and (V) are also equal to H, Y'=S, O or NH, and $L^1$, $L^2$ and $L^3$, independently of one another, are a linear or branched C1-C6-alkyl group, or

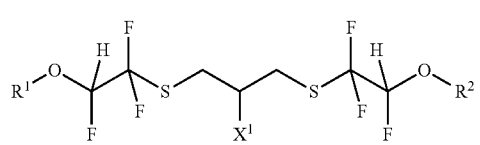
(IV)

where $R^1$ and $R^2$ independently of one another are $CF_3$—$(CF_2)_{1-2}$—, $X^1$=—$SO_3^-$, —$OSO_3^-$, —$COO^-$, —$PO_3^{2-}$, —OP(O)(O$^-$)O—, —$OPO_3^{2-}$, a polyethylene glycol, a polypropylene glycol, —CH(OH)—$CH_2$—NH— sach, —Y'—($CH_2$—$CH_2$—O)$_v$-$R^4$, a betaine, or a sulfobetaine, with counterions being H$^+$, Na$^+$, K$^+$ or NH$_4^+$, sach being a sugar, and Y'=S, O or NH.

2. A compound of formula:

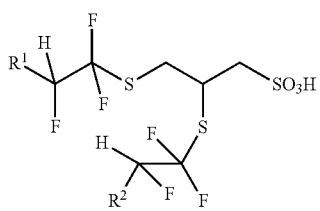
(X)

-continued

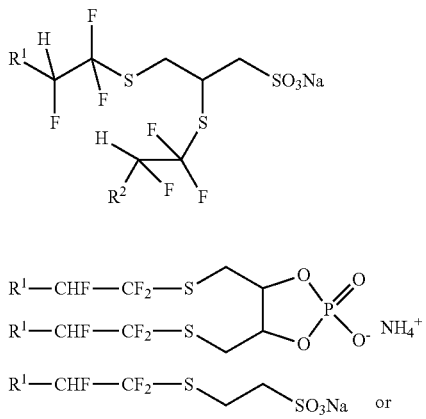
(X')

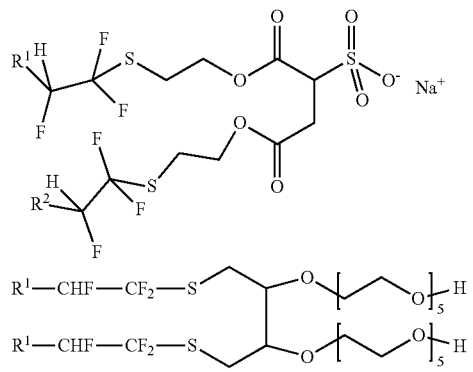
(XIV)

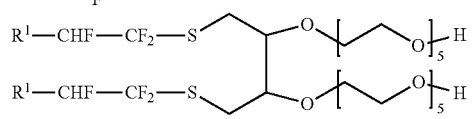

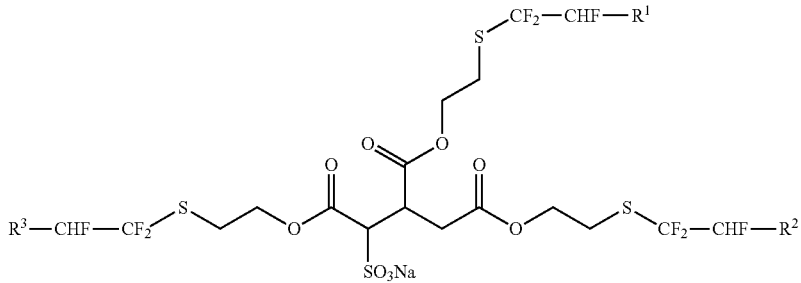

where $R^1$, $R^2$ and $R^3$ are independently $CF_3-(CF_2)_{0-3}-$, $CF_3-(CF_2)_{0-3}-O-$, $CF_3-(CF_2)_{0-3}-O-(CF_2)_{1-3}-$, $CF_3-(CF_2)_{0-3}-O-(CF2)_{1-3}-O-$, $CF_3-(CF_2)_{0-3}-O-(CF_2)_{1-3}-O-CF_2-$, $CF_3-(CF_2)_{0-3}-O-(CF_2-O)_{1-8}$ or $-CF_3-(CF_2)_{0-3}-O-(CF_2-O)_{1-8}-CF_2-$, o is equal to 1-30 and $R^a$, $R^b$ and $R^c$=H or C1-4-alkyl.

3. The compound according to claim 1, of formula:

(XXI)

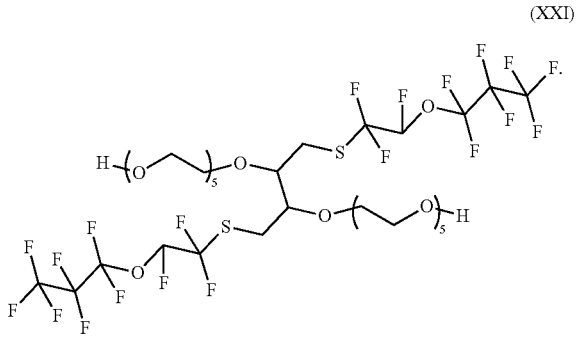

4. A paint, coating, printing ink, protective coating, special coating in electronic or optical applications, photoresist, top antireflective coating or bottom antireflective coating, developer solution, wash solution or photoresist for photolithographic processes, cosmetic product, agrochemical, floor polish, photographic coating or coating of optical elements comprising an additive, wherein the additive is a compound according to claim 1.

5. A composition comprising paint, coating preparations, fire-extinguishing compositions, lubricants, washing or cleaning compositions, de-icers, developer solutions, wash solutions or photoresists for photolithographic processes, cosmetic products, agrochemicals, floor polishes or hydrophobicising compositions for textile finishing or glass treatment, and a compound according to claim 1.

6. The compound according to claim 1, wherein o=5-30.

7. The compound according to claim 1, wherein o=3, 5, 6, 10, 12, 15, 18, 20 or 24.

* * * * *